United States Patent [19]
Pfeiffer

[11] 3,953,422
[45] Apr. 27, 1976

[54] DEOXYGLUCOSE DERIVATIVES

[75] Inventor: Francis R. Pfeiffer, Cinnaminson, N.J.

[73] Assignee: SmithKline Corporation, Philadelphia, Pa.

[22] Filed: Aug. 17, 1973

[21] Appl. No.: 389,091

[52] U.S. Cl. .............................. 260/210 R; 424/180
[51] Int. Cl.² .......................................... C07G 3/00
[58] Field of Search .......... 260/210 R, 211 R, 210 S

[56] References Cited
UNITED STATES PATENTS
3,496,196   2/1970   Suami et al. .................... 260/211 R

OTHER PUBLICATIONS

Wolfrom et al., J. of Org. Chemistry, Vol. 30, pp. 2728–2731, 1965.

*Primary Examiner*—Lewis Gotts
*Assistant Examiner*—Cary Owens
*Attorney, Agent, or Firm*—Stuart R. Suter; Alan D. Lourie; William H. Edgerton

[57] ABSTRACT

3-Deoxyglucose and 3,4-dideoxyglucose derivatives are prepared. They are useful for the preparation of aminoglycosides with antibacterial activity.

31 Claims, No Drawings

DEOXYGLUCOSE DERIVATIVES

This invention relates to 3-deoxyglucose and 3,4-dideoxyglucose derivatives. These chemical intermediates are useful in the preparation of aminoglycoside compounds which have antibacterial activity.

Aminoglycosides are an important group of antibiotics which are prepared by fermentation methods. They have broad spectrum activity; however, resistance has developed as a major problem. One method by which resistance has developed is by enzymatic phosphorylation of the 3′-hydroxy group on the glucose moiety. Removal of the 3′ or 3′,4′-hydroxy groups in natural aminoglycosides has produced compounds which have activity against resistant organisms [*J. Antibiotics*, 24, 274 and 485 (1971)]. In addition, 3′,4′-dideoxyneamine is reported to have activity against resistant organisms while neamine, a major fragment in many aminoglycosides, is inactive against the same organisms [*J. Antibiotics*, 24, 711 (1971)].

This invention discloses intermediates that are useful in preparing 3′-dioxyneamine, 3′,4′-dideoxyneamine, and other analogous deoxyaminoglycosides. These intermediates are also useful for preparing aminoglycoside compounds which contain aminocyclitol moieties different from the naturally-occurring ones.

The 3-deoxyglycose compounds within the scope of this invention are represented by structural formula I.

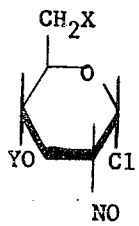

I where
X is OY, NHY, or $N_3$ and
Y is hydrogen or a protecting group.

The 3,4-dideoxyglucose compounds within the scope of this invention are represented by structural formula II.

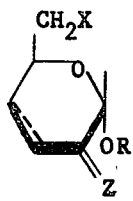

II where
the dotted line is an optional bond;
X is OY, NHY or $N_3$;
Y is hydrogen or a protecting group;
Z is O or NOH; and
R is an aminocyclitol residue.

The compounds of formula I can exist as either a monomer or a dimer which has the following structure:

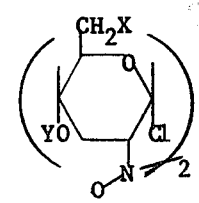

Both monomer and dimer are within the scope of this invention.

Many protecting groups for hydroxy and amino groups are known within the art and compounds of formulas I and II having such groups are within the scope of this invention. For example, useful protecting groups include acetyl, tosyl, benzoyl, benzyl, trityl, methyl, mesyl, dichloroacetyl, 2,4-dinitrophenyl, trichloroethoxycarbonyl, benzyloxycarbonyl, t-butoxycarbonyl, ethoxycarbonyl, tetrahydropyranyl, enamine adduct of dimedone, or other groups known and used in the carbohydrate and peptide synthesis arts. The choice of a protecting group depends on whether a hydroxy or amine group is being protected, subsequent reaction conditions, and conditions for removal; however, this choice is within the ability of one skilled in the art.

The structure of the aminocyclitol residue in formula II is not critical to the invention and can vary widely. Aminoglycoside antibiotics formed by fermentation usually contain streptamine or 2-deoxystreptamine. The formula II intermediates of this invention are not limited to just these cyclitols but may contain any available cyclitol and thereby give aminoglycoside compounds which can not be made by fermentation methods. Examples of cyclitols include 2,5-dideoxystreptamine, 2,5,6-trideoxystreptamine, 4-hydroxycyclohexylamine and the like.

Scheme I outlines one set of reactions that can be used to prepare the 3-deoxyglucose compounds.

SCHEME I

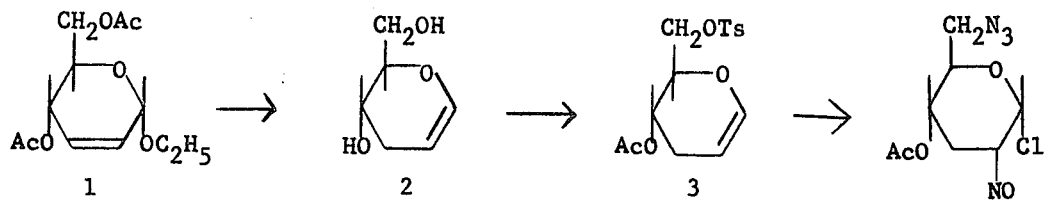

Reduction of the ethyl pyranoside (1) with lithium aluminum hydride gives the glucal (2). Treatment first with p-toluenesulfonyl chloride and then acetic anhydride gives compound 3. Displacement of the tosyl group with azide ion followed by treatment with nitrosyl chloride gives the 3-deoxyglucose derivative 4.

Scheme II exemplifies the use of derivative 4, a compound within the scope of formula I, to prepare amino groups in the glucose moiety may be hydroxyl. For example, if both hydroxyls in compound 2 are protected with the acetyl group and the azide displacement reaction is thus eliminated from the reaction sequence, Scheme I gives 4,6-diacetyl-1-chloro-1,2,3-trideoxy-2-nitroso-D-gluco-pyranose which can be used in the same manner as compound 4. Hydrolysis of the oxime moiety in compounds similar to 6 followed

SCHEME II

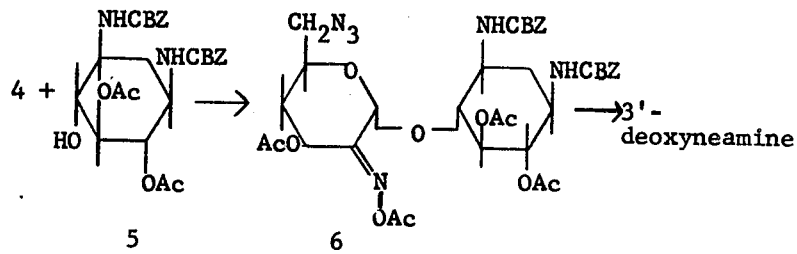

3'-deoxyneamine. Treatment of derivative 4 with a protected derivative of 2-deoxystreptamine (5) followed by acylation of the oxime group gives compound 6. Reduction with diborane and then catalytic hydrogenation gives 3'-deoxyneamine.

By substitution of other suitable cyclitols or aminocyclitols for the 2-deoxystreptamine derivative in Scheme II varied products can be obtained including compounds not available by fermentation. By addition and/or elimination of certain steps, either one or both by reduction of the resultant ketone gives compounds with a 2-hydroxyglucose moiety. Proper choice of reductive conditions will give mostly equatorial hydroxyl groups at position 2 with some mannose derivative being produced. Combination of these two modification gives compounds with the 3-deoxyglucose moiety.

The 3,4-dideoxyglucose compounds, general formula II, may be prepared by a series of reactions as generally outlined in Scheme III.

SCHEME III

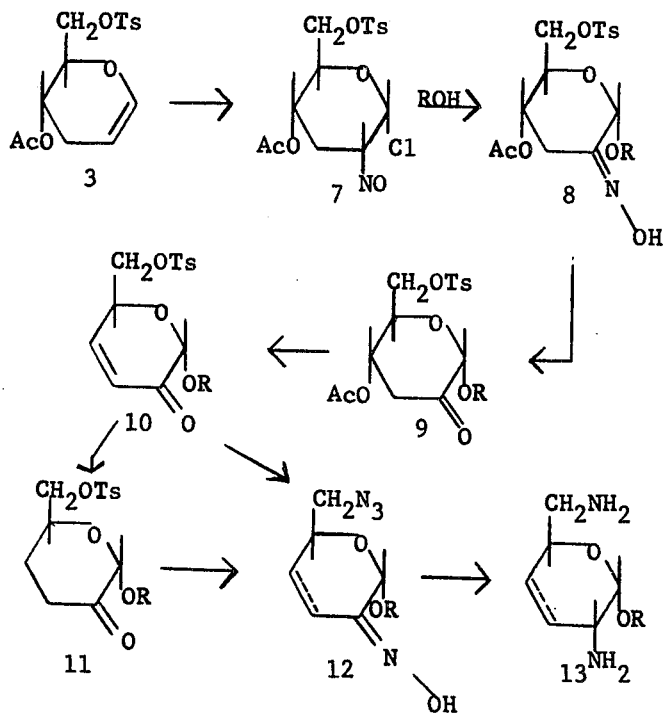

Glucal 3 is treated with nitrosyl chloride to give the adduct 7. A suitably protected cyclitol, for example, the 2-deoxystreptamine derivative 5, is reacted with adduct 7 to give the α-glycoside 8. The α,β-unsaturated ketone 10, a compound within formula II, is prepared by hydrolysis of the oxime to ketone 9 followed by elimination of acetic acid to give compound 10. Compound 11, also within formula II, is obtained by reduction of the double bond.

Compounds 10, 11, and 12 are useful for the preparation of compounds with antibacterial activity. Compound 12 is obtained when compound 10 or 11 is treated with hydroxylamine and then sodium azide. The oxime and azide groups are reduced by standard methods to give the diamino compound 13. When the cyclitol is the 2-deoxystreptamine derivative 5, compound 13 is 3′,4′-dideoxyneamine.

Again, by small changes in the reaction sequence, one or both of the amino groups in compound 13 can be hydroxyl. Reduction of the ketone function in compound 10 or 11 gives a compound similar to 13 but with a 2-hydroxyl group. A 6-hydroxy derivative of 13 is obtained by elimination of the displacement with sodium azide.

The following examples illustrate the invention but are not to be construed as limiting the scope thereof.

PREPARATION 1

4-O-Acetyl-6-O-tosyl-1,2,3-trideoxy-D-erythro-hex-1-enopyranose(3)

A solution of ethyl 4,6-o-acetyl-2,3-dideoxy-α-D-erythro-hex-2-enopyranoside (47.6 g) [J. Chem. Soc., 570 (1969)] in dry dioxane (200 ml) was added dropwise to a hot solution (90°–92°) of LiAlH$_4$ in dry dioxane (900 ml) under a nitrogen atmosphere. After the addition was complete, the reaction mixture was stirred and heated at 95°–98° for 18 hours, cooled, and then treated cautiously with water (80 ml). When all the inorganic salts were hydrolyzed; the white suspension was diluted with ether and filtered. The filtrate was concentrated and azeotroped with dry benzene to give 1,2,3-trideooxy-D-erythro-hex-1-enopyranose (25.6 g). A solution of this diol (25.6g) in dry pyridine (180 ml) was cooled in an ice bath, and treated dropwise with a solution of p-toluenesulfonyl chloride (37 g). Stirring was continued at 0° for 4 hours and at 25° overnight. The mixture was cooled to 0° and treated dropwise with acetic anhydride (30 ml).

After stirring at room temperature for 4 hours, the solution was diluted with ice, concentrated HCl, and ether. The ether layer was separated and washed with dilute HCl, water, 5% NaHCO$_3$, and water. The dried solution was evaporated to give the title product which was recrystallized from ether: 25 g, mp 78°–79°, $[\alpha]_D^{25}$ + 110° (c 1, CHCl$_3$).

PREPARATION 2

4,6-O-Diacetyl-1,2,3-trideoxy-D-erythro-hex-1-enopyranose

A solution of 1,2,3-trideoxy-D-erythro-hex-1-enopyranose (2.56 g) in dry pyridine (18 ml) is cooled to 0° C and treated dropwise with acetic anhydride (5 ml). The reaction is stirred at room temperature for 4 hours, diluted with ice, acidified with HCl, and extracted with ether. The extracts are washed with dilute HCl, water, 5% NaHCO$_3$, and water. The dried ether solution is evaporated to give the title product.

EXAMPLE 1

4O-Acetyl-6-azido-1-chloro-1,2,3,6-tetradeoxy-2-nitroso-D-glucopyranose(4)

To a solution of 4-O-acetyl-6O-tosyl-1,2,3-tri-deoxy-D-erythro-hex-1-enopyranose (9.75 g) in hexamethylphosphoramide (150 ml) was added sodium azide (19.4 g). The mixture was stirred at room temperature for 4 hours, diluted with cold brine solution (1 l) and extracted with ether. The extracts were washed with dilute HCl, 5% NaHCO$_3$, and brine. Evaporation of the dried extracts gave the crude 6-azido derivative which was chromatographed on a Florisil column using increasing amounts of benzene in petroleum ether (20–70%) as eluent: 4.2 g, $[\alpha]_D^{25}$ + 149.7° (c 1, CHCl$_3$).

The above product (9.2 g) was dissolved in dry ethyl acetate (120 ml) and a stream of nitrosyl chloride was passed slowly through the solution at −40° for 15 minutes. Nitrogen was bubbled through the solution as it was allowed to warm to 0° over a 25-minute period. The solvent was evaporated in vacuo at <25° to give the title compound as a dimer.

EXAMPLE 2

4(6)-5,6-O-Diacetyl-1,3-dicarbobenzyloxy-2-deoxystreptamine
4-O-acetyl-6-azido-3,6-dideoxy-2-acetyloximino-α-D-glucopyranoside (6)

A solution of 1,3-dicarbobenzyloxy-5,6-diacetyl-2-deoxystreptamine (15.7 g) in dry dimethylformamide (140 ml) was added to 4-O-acetyl-6-azido-1-chloro-1,2,3,6-tetradeoxy-2-nitroso-glucopyranose (8.4 g). The solution was stirred at room temperature for 48 hours and then diluted with ice water (1.5 l). The oximino product was extracted into ethyl acetate which was dried and concentrated to a syrup. This product was acylated in pyridine (60 ml) with acetic anhydride (40 ml) by the procedure used in Preparation 1. The solid product was chromatographed on a Florisil column (750 g) with a petroleum ether — ethyl acetate gradient as eluent: mp. 190°–2°$[\alpha]_D^{25}$ + 100.4° (c 1, CHCl$_3$).

EXAMPLE 3

3′-deoxyneamine

The oxime acetate from Example 2 (4.8 g) was dissolved in dry tetrahydrofuran (120 ml), cooled to −10° and maintained under a nitrogen atmosphere. A 1M solution of diborane in THF (60 ml) was added dropwise. The solution was allowed to warm to room temperature and then stirred an additional 3 hours. Methanol (100 ml) was added cautiously and the solution was evaporated to a residue which was dissolved in methanol (150 ml) and treated for 20 minutes with 400 ml of polystyrene quaternary ammonium resin [Amberlite IR 400 (OH⁻)]. After filtration, the filtrate was evaporated to a syrup which was dissolved in acetic acid (12 ml) and methanol (12 ml) and hydrogenated for 18 hours at 60 psi with 10% palladium on charcoal (2.5 g). Evaporation of the filtered solution gave the crude title product which was chromatographed on a polystyrene basic resin [Dowex 1×2 (OH⁻)] with water as eluent. The sulfate salt was prepared by adjusting an aqueous solution of the product to pH 3.5 with dilute sulfuric acid. Lyophilization gave 3′-deoxyneamine sulfate, mp 250°–5°, $[\alpha]_D^{25} + 48°$ (c 0.5, $H_2O$).

EXAMPLE 4

4-(1,3-dicarbobenzyloxy-5,6-diacetyl-2-deoxystreptamine)
 4-acetyl-3-deoxy-2-oximino-6-O-tosyl-D-erythropyranoside (8)

A solution of 4-O-acetyl-1,2,3-trideoxy-6-O-tosyl-D-hex-1-enopyranose (1.89 g) in dry ethyl acetate (35 ml) was reacted with nitrosyl chloride and the product, 4-O-acetyl-1-chloro-1,2,3-trideoxy-2-nitroso-6-O-tosyl-D-glucopyranose was isolated by the procedure used in Example 1. The nitrosyl chloride product was dissolved in dry, freshly distilled dimethylformamide (10 ml) and then 1,3-dicarbobenzyloxy-5,6-diacetyl-2-deoxystreptamine (2 g, 0.66 equiv.) was added. The solution was stirred at room temperature for 48 hours, diluted with ice water, and extracted with ethyl acetate. The dried extracts were concentrated to a residue which was chromatographed on Florisil (120 g) with an ethyl acetate — cyclohexane gradient as eluent, mp. 148°–150° $[\alpha]_D^{25} + 56°$ (c 1, $CHCl_3$).

EXAMPLE 5

4-(1,3-dicarbobenzyloxy-5,6-diacetyl-2-deoxystreptamine)
 3,4-dideoxy-2-keto-6O-tosyl-α-D-hexopyranoside(11)

A solution of the product from Example 4 (3.0 g) in acetonitrile (25 ml) and tetrahydrofuran (25 ml) was treated with 1N HCl (2.5 ml) and acetaldehyde (2.5 ml) at room temperature for 6 hours. The solution was diluted with ethyl acetate (300 ml) and water (50 ml). The organic phase was separated, washed with brine, dried, and concentrated to the 2-keto derivative (3g). The ketone in dry benzene (30 ml) and alcohol-free chloroform (30 ml) was stirred with neutral alumina (10 g) (Woehlm activity III) at room temperature until tlc indicated that the reaction was completed. The solvent was evaporated and the crude α,β-unsaturated ketone was immediately dissolved in ethyl acetate (100 ml) and hydrogenated at 45 psi with 10% palladium on charcoal (1.5 g). Filtration and evaporation gave the diaminoketone which was treated with excess benzyl chloroformate and sodium bicarbonate in aqueous dioxane to give the title product, mp 132°–4°, $[\alpha]_D^{25}$ +77° (c 1, $CHCl_3$).

EXAMPLE 6

3′,4′-dideoxyneamine(13)

The product of Example 5 was converted to the 2′-oxime by treatment with methanolic hydroxylamine. The oxime was treated with a 10 molar excess of sodium azide in hexamethylphosphoramide for 18 hours at room temperature. The solution was diluted with water and extracted with ethyl acetate. The extracts were washed with water, dried, and concentrated to a product which was reduced first with diborane for 16 hours and then with catalytic hydrogenation; both reductions were done according to the procedures given in Example 3. The title product was purified over Amberlite IR 50 ($NH_4^+$) using a gradient of 0.05 to 0.5 ammonium hydroxide as eluent, $[\alpha]_D^{25} + 92°$ (c 1, $H_2O$).

EXAMPLE 7

4,6O-Diacetyl-1-chloro-1,2,3-trideoxy-2-nitroso-D-glucopyranose

A solution of 4,6-O-diacetyl-1,2,3-trideoxy-D-erythro-hex-1-enopyranose in dry ethyl acetate is treated with nitrosyl chloride according to the procedure in Example 1 to give the title product.

EXAMPLE 8

4-(1,3-Dicarbobenzyloxy-5,6-diacetyl-2-deoxystreptamine)
 6-O-acetyl-3,4-dideoxy-2-keto-α-D-hexopyranoside Treatment of 4,6-O-diacetyl-1,2,3-tridoxy-D-erythro-hex-1-enopyranose with nitrosyl chloride and then with 1,3-dicarbobenzyloxy-4,6-diacetyl-2-deoxystreptamine according to the procedure in Example 4 gives 4-(1,3-dicarbobenzyloxy-5,6-diacetyl-2-deoxystreptamine) 4,6-O-diacetyl-3-deoxy-2-oximino-D-erythropyranoside. When this product is substituted as starting material in Example 5, 4-(1,3-dicaroben-zyloxy-5,6-diacetyl-2-deoxystreptamine) 6-O-acetyl-3,4-dideoxy-2-keto-α-D-hexopyranoside is obtained.

EXAMPLE 9

When 1,3-dicarbobenzyloxy-2,5,6-triacetylstreptamine, 1,3-dicarbobenzyloxy-6-acetyl-2,5-dideoxystreptamine, 1,3-dicarbobenzyloxy-2,5,6-trideoxystreptamine, or trans-N-acetyl-4-hydroxycyclohexylamine is substituted for 1,3-di-carbobenzyloxy-5,6-diacetyl-2-deoxystreptamine in Example 4 the following products are obtained:
4-(1,3-dicarbobenzyloxy-2,5,6-triacetylstreptamine) 4-O-acetyl-3-deoxy-2-oximino-6-O-tosyl-D-erythro-pyranoside
4-(1,3-dicarbobenzyloxy-6-acetyl-2,5-dideoxystreptamine) 4-O-acetyl-3-deoxy-2-oximino-6-O-tosyl-D-erythro-pyranoside
4-(1,3-dicarbobenzyloxy-2,5,6-trideoxystreptamine) 4-O-acetyl-3-deoxy-2-oximino-6-O-tosyl-D-erythro-pyranoside
trans-4-acetamidocyclohexyl 4O-acetyl-3-deoxy-2-oximino-6-O-tosyl-D-erythro-pyranoside

EXAMPLE 10

The products of Example 9 are reacted according to the procedure of Example 5 to give the following products:
4-(1,3-dicarbobenzyloxy-2,5,6-triacetylstreptamine) 3,4-dideoxy-2-keto-6-O-tosyl-α-D-hexopyranoside
4-(1,3-dicarbobenzyloxy-6-acetyl-2,5-dideoxystreptamine)3,4-dideoxy-2-keto-6-O-tosyl-α-D-hexopyranoside
4-(1,3-dicarbobenzyloxy-2,5,6-trideoxystreptamine) 3,4-dideoxy-2-keto-6-O-tosyl-α-D-hexopyranoside
trans-4-acetamidocyclohexyl 3,4-dideoxy-2-keto-6-O-tosyl-α-D-hexopyranoside

EXAMPLE 11

The α,β-unsaturated ketone prepared in Example 5 is treated immediately after isolation with methanolic hydroxylamine at room temperature and in the presence of sodium acetate. The reaction mixture is poured into water and the aqueous solution extracted with ethyl acetate. The dried extracts are evaporated to give the α,β-unsaturated oxime.

I claim:

1. A compound of the formula

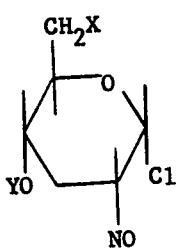

where
X is OY, NHY, or $N_3$; and
Y is hydrogen or a hydroxy protecting group or amino protecting group,
or a dimer of said compound, said dimer having the formula

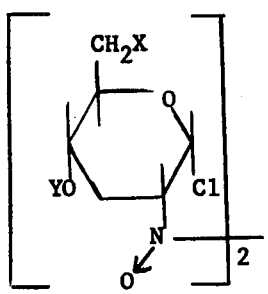

2. A compound as claimed in claim 1 where Y is hydrogen, acetyl, tosyl, benzoyl, benzyl, trityl, methyl, mesyl, dichloroacetyl, 2,4-dinitrophenyl, trichloroethoxycarbonyl, benzyloxycarbonyl, t-butoxycarbonyl, ethoxycarbonyl, tetrahydropyranyl, or enamine adduct of dimedone.

3. A compound as claimed in claim 2 where X is OY.

4. A compound as claimed in claim 2 where X is NHY.

5. A compound as claimed in claim 2 where X is $N_3$.

6. A compound as claimed in claim 5 being the compound 4O-acetyl-6-azido-11-chloro-1,2,3,6-tetradeoxy-2-nitroso-D-glucopyranose.

7. A compound as claimed in claim 3 being the compound 4O-acetyl-1-chloro-1,2,3-trideoxy-2-nitroso-6-O-tosyl-D-glucopyranose.

8. A compound of the formula

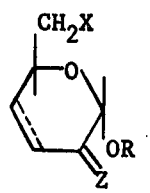

where
the dotted line is an optional carbon-carbon bond;
X is OY, NHY, or $N_3$;
Y is hydrogen or a hydroxy protecting group or amino protecting group;
Z is O or NOH; and
R is a aminocyclitol residue.

9. A compound as claimed in claim 8 where Y is hydrogen, acetyl, tosyl, benzoyl, benzyl, trityl, methyl, mesyl, dichloroacetyl, 2,4-dinitrophenyl, trichloroethoxycarbonyl, benzyloxycarbonyl, t-butoxycarbonyl, ethoxycarbonyl, tetrahydropyranyl, or enamine adduct of dimedone.

10. A compound as claimed in claim 9 where the optional carbon-carbon bond is present.

11. A compound as claimed in claim 9 where the optional carbon-carbon bond is not present.

12. A compound as claimed in claim 10 where X is OY.

13. A compound as claimed in claim 10 where X is NHY.

14. A compound as claimed in claim 10 where X is $N_3$.

15. A compound as claimed in claim 11 where X is OY.

16. A compound as claimed in claim 11 where X is NHY.

17. A compound as claimed in claim 11 where X is $N_3$.

18. A compound as claimed in claim 12 where Z is O.

19. A compound as claimed in claim 12 where Z is NOH.

20. A compound as claimed in claim 13 where Z is O.

21. A compound as claimed in claim 13 where Z is NOH.

22. A compound as claimed in claim 14 where Z is O.

23. A compound as claimed in claim 14 where Z is NOH.

24. A compound as claimed in claim 15 where Z is O.

25. A compound as claimed in claim 15 where Z is NOH.

26. A compound as claimed in claim 16 where Z is O.

27. A compound as claimed in claim 16 where Z is NOH.

28. A compound as claimed in claim 17 where Z is O.

29. A compound as claimed in claim 17 where Z is NOH.

30. A compound as claimed in claim 15 being the compound 4-(1,3-dicarbobenzyloxy-5,6-diacetyl-2-deoxystreptamine) 3,4-dideoxy-2-keto-6-O-tosyl-α-D-hexopyranoside.

31. A compound as claimed in claim 15 being the compound 4-(1,3-dicarbobenzyloxy-5,6-diacetyl-2-deoxy-streptamine) 3,4,6-trideoxy-2-keto-6-azido-α-D-hexo-pyranoside.

* * * * *

UNITED STATES PATENT AND TRADEMARK OFFICE
CERTIFICATE OF CORRECTION

PATENT NO. : 3,953,422
DATED : April 27, 1976
INVENTOR(S) : Francis R. Pfeiffer

It is certified that error appears in the above-identified patent and that said Letters Patent are hereby corrected as shown below:

Column 1, line 23: "3'-dioxyneamine" should read
-- 3'-deoxyneamine --

Column 8, line 31: "dicaroben" should read -- dicarboben --

Column 9, in claim 6: The compound name should read -- 4-O-acetyl-6-azido-1-chloro-1,2,3,6-tetradeoxy-2-nitroso-D-glucopyranose --

Column 9, in claim 7: The compound name should read
-- 4-O-acetyl-1-chloro-1,2,3-trideoxy-2-nitroso-6-O-tosyl-D-glucopyranose --

Signed and Sealed this

Twenty-first Day of September 1976

[SEAL]

Attest:

RUTH C. MASON
*Attesting Officer*

C. MARSHALL DANN
*Commissioner of Patents and Trademarks*